(12) United States Patent
Wulf et al.

(10) Patent No.: US 6,211,989 B1
(45) Date of Patent: Apr. 3, 2001

(54) LIGHT-SCANNING DEVICE

(75) Inventors: Jürgen Wulf, Ueberlingen; Michael Steinwand, Owingen; Henry Klemm, Ueberlingen, all of (DE)

(73) Assignee: Bodenseewerk Perkin-Elmer GmbH, Ueberlingen (DE)

( * ) Notice: Subject to any disclaimer, the term of this patent is extended or adjusted under 35 U.S.C. 154(b) by 0 days.

(21) Appl. No.: 09/367,949

(22) PCT Filed: Dec. 4, 1997

(86) PCT No.: PCT/EP97/06793

§ 371 Date: Dec. 17, 1999

§ 102(e) Date: Dec. 17, 1999

(87) PCT Pub. No.: WO98/38495

PCT Pub. Date: Sep. 3, 1998

(30) Foreign Application Priority Data

Feb. 24, 1997 (DE) .............................. 197 07 226

(51) Int. Cl.⁷ .................................................. G02B 26/08
(52) U.S. Cl. ........................ 359/210; 359/209; 356/317
(58) Field of Search .................................. 359/209, 210; 356/317, 318, 319, 320

(56) References Cited

U.S. PATENT DOCUMENTS 4,626,684 * 12/1986 Landa ..................................... 356/318
5,022,757 * 6/1991 Modell ................................. 356/318

FOREIGN PATENT DOCUMENTS 504 432 * 9/1992 (EP) .
753 779 * 1/1997 (EP) .
96/09548 * 3/1996 (WO) .

* cited by examiner

Primary Examiner—Darren Schuberg
(74) Attorney, Agent, or Firm—Perman & Green, LLP

(57) ABSTRACT

A light scanning device for exciting and detecting secondary light, especially fluorescent light, on a sample, comprising a light emission device for emitting exciting light with a wavelength suitable for exciting secondary light on or in said sample, a focussing optics for focussing the exciting light on a subarea of said sample, a sample holding device for releasably holding the sample, a detection unit comprising a detection optics for the secondary light emitted by the sample in response to excitation and a detector device for converting the detected and imaged secondary light into electric signals. In the case of conventional known light scanning devices, scanning is carried out by means of a deflection unit consisting of tilting mirrors. Due to the long path of the light beam, positioning inaccuracies of the tilting mirrors result in major position inaccuracies of the scanning ray bundle on the surface of the sample. For avoiding this disadvantage of the prior art, the light scanning device according to the present invention makes use of a sample holding device which is adapted to be rotated for rotating the sample relative to the exciting light in such a way that different subareas of said sample can be excited by means of the exciting light so as to emit secondary light. Due to the mechanical rotary movement of the sample, a deflection of the scanning light beam relative to the optical axis is not necessary so that precise positioning of the scanning ray bundle on the sample is possible.

15 Claims, 2 Drawing Sheets

LIGHT-SCANNING DEVICE

FIELD OF THE INVENTION

The present invention relates to a light scanning device for exciting and detecting secondary light, especially fluorescent light, on a sample, comprising a light emission device for emitting exciting light with a wavelength suitable for exciting secondary light on or in said sample, a focussing optics for focussing the exciting light on said sample, a sample holding device for releasably holding the sample, a detection unit comprising a detection optics for the secondary light emitted by the sample in response to excitation and a detector device for converting the secondary light into electric signals.

BACKGROUND ART

Such light scanning devices are used e.g. for examinations in the field of molecular biology or genetic technology. For these examinations, a large number of materials to be examined are applied to a carrier in a fieldlike configuration, whereupon said materials are temporarily brought into contact with a fluorescent tracer. The materials to be examined having an affinity for the tracer will bind said tracer to themselves and can therefore be excited so as to emit fluorescent light. It follows that, due to the excitability of the fluorescence, the property of the examined material to bind to itself the tracer becomes visible, whereby it is possible to draw conclusions with regard to the nature of the sample material.

When examinations in the field of molecular biology or genetic technology are carried out, large fields of such materials marked with fluorescent substances are sequentially scanned with exciting light. In hitherto known devices, the carrier holding the sample materials has been scanned by means of two tilting mirrors provided in the optical path of the exciting light, the two axes of rotation of said tilting mirrors extending at right angles to one another. When the scanning light beam impinges on a location where a marked and, consequently, fluorescent sample material is present secondary light will be emitted, which is detected by a detection unit comprising a detection optics and a detector device, and converted into electric signals.

In such devices the rotation of the tilting mirrors for the purpose of scanning is, however, subject to tolerances, and due to the long beam path this results in major inaccuracies in the local resolution of the scanning. In the case of a "pre-objective-scanning" arrangement of the focussing optics (i.e. between the scanning unit and the sample), it is additionally necessary that said focussing optics has a large diameter so that an image of the light ray bundle deflected from the optical axis by the scanning mirrors can be formed in the plane of the sample. When such large-diameter lenses are used, a correction for large angular fields and a good field flatness is, however, very complicated and entails therefore higher costs.

SUMMARY OF THE INVENTION

It is therefore an object of the present invention to provide a light scanning device of the type mentioned at the beginning, by means of which an improved local resolution can be achieved on the basis of a simplified structural design.

According to the present invention, this object is achieved by a light scanning device of the type mentioned at the beginning, which is characterized in that the sample holding device is adapted to be rotated for rotating the sample relative to the exciting light in such a way that different subareas of said sample can be excited by means of the exciting light so as to emit secondary light.

According to the present invention, this object is additionally achieved by a light scanning device of the type mentioned at the beginning, which is characterized in that the focussing optics is rotatably supported so as to conduct the exciting light along a circular arc on the sample.

According to these two solutions, the hitherto known scanning system making use of tilting mirrors is replaced by a mechanical rotation of either the sample or the scanning light beam, a circular arc on the surface of the sample being scanned in both cases. An increase of inaccuracies and tolerances, respectively, which occurs according to the galvanometer principle when the tilting mirrors are rotated in the hitherto known scanning devices and which results in comparatively large inaccuracies of the position coordinates of the scanning beam on the sample, is excluded in the device according to the present invention, since the beam axis is not tilted relative to the sample surface. Devices according to the present invention can therefore achieve high local resolutions of up to 2 $\mu$m, e.g. in cases where a suitable laser diode is used as a light emission device. In addition, the focussing optics used for focussing the exciting light onto a subarea of the sample can consist of a comparatively economy-priced lens having a small diameter and a small corrected field area. The device according to the present invention permits therefore a substantial reduction of costs due to the fact that a simple and inexpensive focussing optics is used and that the complicated holding and control means for the tilting mirrors can be dispensed with.

According to an advantageous further development of the present invention, the focussing optics is adapted to be radially displaced relative to the axis of rotation of the sample holding device or the sample holder is adapted to be displaced in the radial direction relative to the optical axis of the focussing optics. A two dimensional local resolution by means of a simple mechanical movement of the focussing optics and of the sample holder, respectively, is achieved in this way, without changing the angle of the beam axis relative to the surface of the sample. It follows that, according to this advantageous further development, the very good local resolution is achieved also in the second dimension. The above-mentioned economy-priced lens having a small diameter and requiring little expenditure with regard to, field correction can also be used in this embodiment.

According to another advantageous further development, two or more respectively associated pairs of the focussing optics and of the detection unit are provided. This permits a substantial reduction of the scanning time, especially in cases where large samples and a high resolution are used. When two focussing optics and detection unit pairs are used, the scanning time of the sample surface will be halved. The optical paths of the two focussing optics and detection unit pairs should preferably extend at a distance from one another which corresponds to half the radius of the total area scanned. In particular, it will be advantageous when said focussing optics and detection unit pairs are mechanically coupled. In this case, adjusting elements for radially displacing the focussing optics can be dispensed with due to the mechanical coupling, and this will, in turn, reduce the costs of the light scanning device according to the present invention, and, in addition, a more precise positioning will be guaranteed due to the rigid mechanical connection.

When a plurality of detectors is used simultaneously, it will be advantageous to provide pinhole diaphragms in a respective imaging plane of a detection optics in front of the detector device in question. This will prevent crosstalk between the individual detectors and an acceptance of stray light from the surroundings of the exciting light spot.

Finally, a plurality of light sources with different emission light wavelengths and/or colour filters of different transmission wavelengths can be provided in front of the individual detector devices in the light scanning device according to the present invention, whereby the flexibility and the versatility of the system will be increased.

Further advantageous embodiments are disclosed in the sub-claims.

BRIEF DESCRIPTION OF THE DRAWINGS

Making reference to a preferred embodiment as an example, the present invention will be explained and described in more detail in the following. In the accompanying drawings.

FIG. 1 shows a schematic representation of an embodiment of the light scanning device according to the present invention. A light emission device 10, which can, for example, be a laser, emits a light beam 11 which falls upon a first unit 30 including a focussing optics for the light beam and a detection optics for the secondary light. The first unit 30 includes a support body 35 supporting a beam splitter cube 33, a focussing lens 34 for focussing the light emitted by the light emission device 10 onto the sample, a detection lens 32 for detecting and collecting secondary light and a detector 31. The support body 35 is provided with openings along the propagation path of the emitted light ray bundle 11, which permit said light ray bundle 11 to pass. The beam splitter 33 is arranged in the optical path of the light ray bundle 11 in such a way that part of the ray bundle 11 is reflected substantially at right angles, whereupon it proceeds along an optical axis 12 extending through the focussing lens 34. The part of the ray bundle transmitted through the beam splitter 33 leaves the support body 35 at a corresponding second opening and impinges on a second unit 40 whose structural design is essentially identical to that of the first unit 30.

Figure 1:
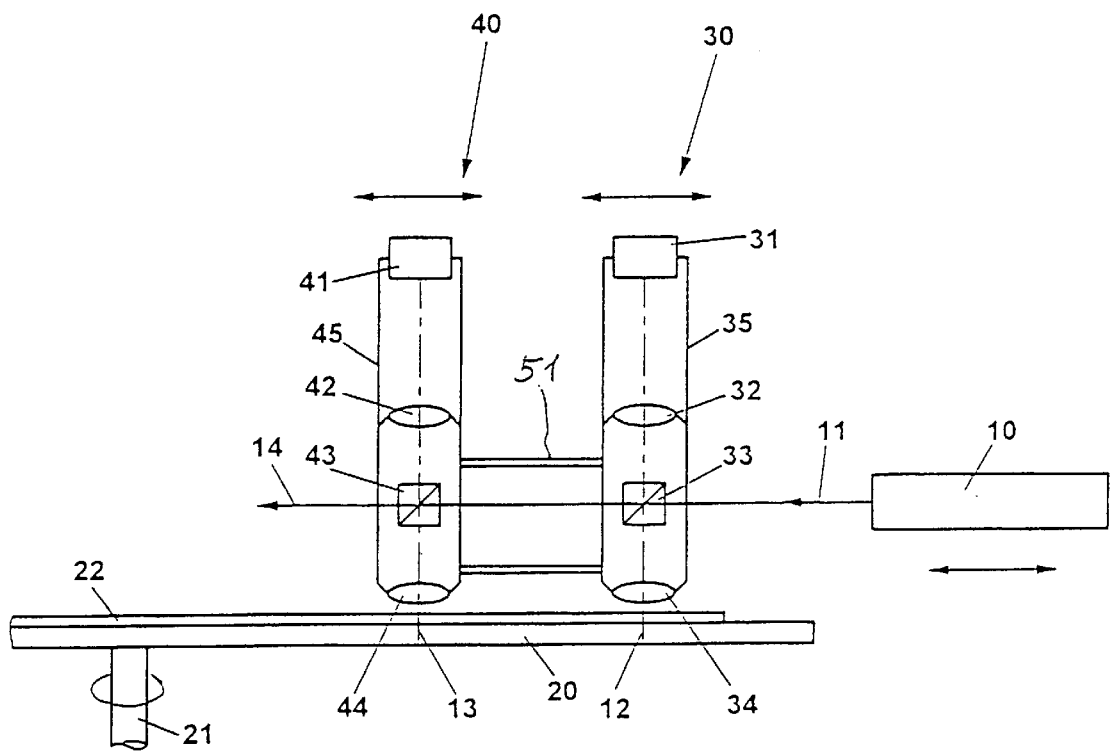
FIG. 1 shows a schematic view of a structural design of an embodiment according to the present invention.

Hence, the second unit 40 comprises a detector 41, a detection lens 42 for detecting and collecting the secondary light, a beam splitter 43 and a focussing optics 44, all these components being supported in a support body 45. The support body 45 is again provided with suitably arranged openings through which the ray bundle 11, which is produced by the light emission device 10 and which progresses in straight lines, enters and leaves said support body.

In the embodiment shown, the two units 30 and 40 are mechanically coupled by means of a rigid connection 51. As indicated by the horizontal arrows, the units 30 and 40 are adapted to be displaced in common along the direction of propagation of the non-deflected ray bundle 11 emitted by the emission device 10.

A sample 22, which is releasably held on a sample holder 20, is arranged in opposed relationship with the two focussing lenses 34 and 44. In the embodiment shown, the sample holder 20 is a rotary table supported on a rotary shaft 21. For holding the sample 22 on the rotary table 20, fixing elements or vacuum suction lines, which are not shown, can be provided; in most cases, the normal friction of the sample on the support will, however, suffice.

In the embodiment shown in FIG. 1, the distance between the units 30 and 40 corresponds to half the radius of the area to be scanned on the sample 22.

The optical path of the light ray bundle 11 emitted by the light emission device 10 extends first essentially parallel to the surface of the sample 22 and is deflected at the respective beam splitters 33 and 43 in a direction substantially at right angles to the surface of the sample 22 so as to focus the exciting light via the focussing lenses 34 and 44 onto two points of the sample surface. The secondary light emitted by the sample surface in the case of fluorescence proceeds into the upper semispace (provided that the sample holder 20 absorbs). The part of this secondary light used for the detector is only the part which can be accepted by the optics 34, 32 and 44, 42, respectively. After having been collected by the focussing lenses 34 and 44, the secondary light proceeds to the beam splitters 33 and 43. At the beam splitters 33 and 43, the optical paths, which are united for the exciting light and the secondary light between the sample 22 and the two beam splitters, are separated. Part of the secondary light is reflected at the beam splitters 33 and 43 in the direction of the light emission device 10, whereas another part passes through the beam splitter cubes and impinges on the respective detection lenses 32 and 42 which image the secondary light on the respective detectors 31 and 41.

The beam splitter cube used may be a polarizing cube which reflects a polarized exciting light with high reflectivity in the direction of the samples. The fluorescent molecules are distributed satistically ("randomly") and emit in all directions of polarization. The amount of light reflected in the direction of the light emission device 10 is therefore only small, whereas most of the light passes through the beam splitter.

In the embodiment shown, where two units 30 and 40 are used, the beam splitters have, for example, a splitting ratio of 50:50.

Figure 2:
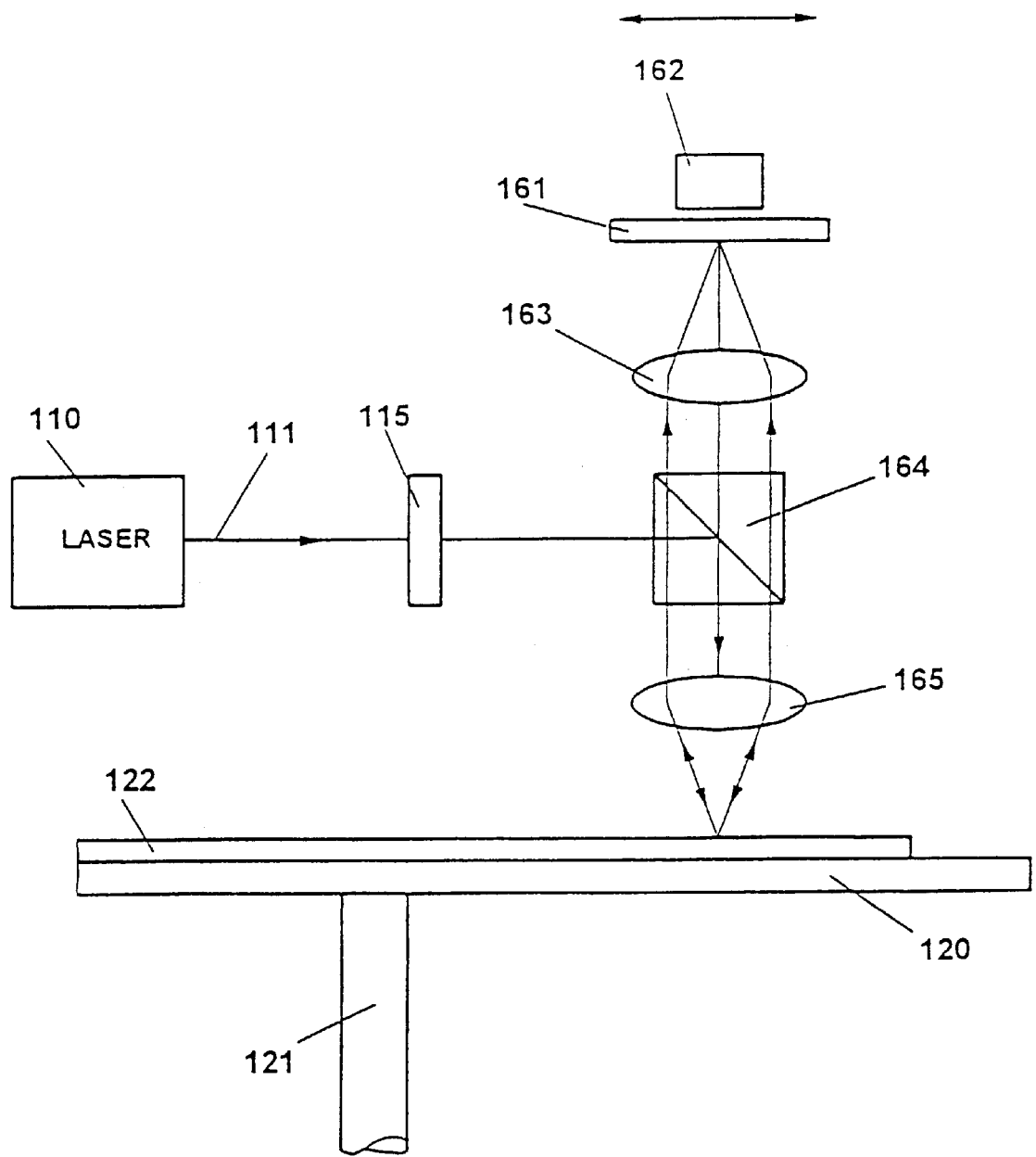
FIG. 2 shows a schematic representation of a further embodiment of the present invention.

In FIG. 2, a further embodiment of the light scanning device according to the present invention is shown. A light emission device 110, e.g. a laser, produces an exciting light ray bundle 111 which falls upon a schematically shown beam expansion optics 115 used for expanding the exciting light ray bundle. The beam expansion optics 115 can also include a spatial filter for improving the beam quality. Subsequently, a dichroic beam splitter 164 follows in the optical path of the exciting light beam, said dichroic beam splitter reflecting the exciting light almost completely at right angles in the direction of a sample 122. Between the beam splitter and the sample 122, a focussing lens 165 is arranged, which focusses the exciting light onto a small spot on the sample.

As in the case of the preceding embodiment, the sample 122 is again releasably attached to a rotary table 120, which is rotatably supported via rotary shaft 121.

The first element in the optical path of the fluorescent light emitted by the sample 122 is the focussing optics 165, said focussing optics 165 being followed by the dichroic beam splitter 164 which is designed in such a way that the fluorescent light whose wavelength differs from that of the exciting light is transmitted almost completely to a detection optics 163 focussing the fluorescent light onto a pinhole diaphragm 161 behind which a detector 162 is arranged.

In addition to the elements of the above-described embodiments shown in FIG. 1 and 2, a blocking filter can be provided in front of the respective detectors so as to suppress stray light from the light emission device. By means of the blocking filter and the pinhole diaphragm (which can, of course, also be provided in front of the detectors 31 and 41 of the embodiment shown in FIG. 1) a strong suppression of scattered exciting light is achieved and the signal-to-noise ratio is noticeably improved. In the embodiment shown in FIG. 2, the focussing lens 165 can be displaced together with the beam splitter 164, the detection lens 163, the pinhole diaphragm 161 and the detector 162 along the optical axis of the exciting light ray bundle 111 between the light generation device and the beam splitter.

It would also be possible to use an emission filter at the pinhole diaphram 161 so as to select the wavelength of the emitted light.

In the two embodiments shown, it would also be possible to exchange the positions of the laser and of the detection optics while reorientating the beam splitter in a suitable manner. Furthermore, it would be possible to provide, instead of the rotary movement of the sample holder and the linear movement of the focussing and detection unit, the rotary movement in the case of the latter and to arrange the sample such that it is linearly displaceable, whereby it would again be possible to raster the whole sample area.

In the embodiments shown, it would also be possible to arrange the light emission device and/or the detection unit(s) in a fixed manner and to couple the light via flexible optical fibres to the displaceable focussing optics. When optical fibres are used for coupling in the exciting light and for transmitting the fluorescent light emitted by the sample to the detector, the beam splitter could be dispensed with. Such a use of optical fibres in the case of the embodiment shown in FIG. 1 permits a fixed arrangement of the detectors 31 and 41 with regard to the displacement motion of the focussing lens; a flexible connection between the detectors and the focussing optics would then be established by means of the optical fibres.

When a plurality of focussing and detection units is used, it will also be possible to provide different wavelength filters in front of the respective detectors, whereby different fluorophores or various wavelengths of the same fluorescent dye can be measured simultaneously. On the other hand, different light emission devices can be provided, which are each coupled in via a separate ray path and which have different excitation wavelengths for exciting different fluorescent dyes. It is in this way also possible to measure the sample simultaneously with regard to different dyes.

Instead of the reflective arrangements shown in FIG. 1 and 2, an arrangement for measurement in transmission would be imaginable as well. In this case, the respective beam splitter cubes would be dispensed with and the detection units would be arranged on the side of the sample and on the side of the in this case transparent sample holder located opposite the excitation side. The detection optics would then be coupled in a suitable manner with the linear movement of the exciting light bundle(s) on the sample 22.

Especially in cases where one or a plurality of laser diodes is used as a light emission device, the use of a beam shaping optics, which is symbolically indicated by reference numeral 115 in FIG. 2, will be advantageous.

The sample is applied to a carrier by means of a microspot application method, said carrier being releasably attached to the sample holder. The carrier can be a circular disk or it may also have an arbitrary other flat shape. For applying the sample to the carrier, microdosing techniques can be used, making use e.g. of a microdrop piezotechnology. This technology permits the application of individual spot samples whose diameter ranges typically from 30 to 100 μm.

The present invention provides the essential advantage that, due to the rotary movement and the linear movement, respectively, the positioning of the scanning light bundle on the sample can be controlled more precisely than by means of tilting the tilting mirrors according to the prior art, where an increase of the position tolerance occured as in the case of a mirror galvanometer. Due to the use of a plurality of detectors, the scanning time can be reduced substantially, the rigid connection of the imaging and detection optics resulting in an improvement of the positioning. The pinhole diaphragms arranged confocally in front of the detectors prevent a cross-talk between the channels associated with the two detectors and suppress stray light from the surroundings of the exciting light spot, whereby the signal-to-noise ratio is improved. The possibility of using a plurality of light emission devices and various filters improves the flexibility of the system.

What is claimed is:

1. A light scanning device for exciting and detecting secondary light, especially fluorescent light, on a sample (22), comprising
   a light emission device (10) for emitting exciting light (11) with a wavelength suitable for exciting secondary light on or in said sample (22),
   a focussing optics (34, 44) for focussing the exciting Light on a subarea of said sample (22),
   a sample holding device (20, 21) for releasably holding the sample (22), and
   a detection unit comprising a detection optics (32, 42) for the secondary light emitted by the sample in response to excitation and a detector device (31, 41) for converting the detected and imaged secondary light into electric signals,
   wherein the sample holding device is adapted to be rotated for rotating the sample relative to the exciting light so that different subareas of said sample can be excited by means of the exciting light so as to emit secondary light, and
   there are at least two respectively associated pairs of said focussing optics and said detection units.

2. A light scanning device for exciting and detecting secondary light, especially fluorescent light, on a sample (22), comprising
   a light emission device (10) for emitting exciting light (11) with a wavelength suitable for exciting secondary light, on or in said sample (22),
   a focussing optics (34, 44) for focussing the exciting light on a subarea of said sample (22),
   a sample holding device (20, 21) for releasably holding the sample (22), and
   a detection unit comprising a detection optics (32, 42) for the secondary light emitted by the sample in response to excitation and a detector device (31, 41) for converting the detected and imaged secondary light into electric signals,
   wherein the focussing optics (34, 44) is rotatably supported so as to conduct the exciting light along a circular arc on the sample, and
   there are at least two respectively associated pairs of said focussing optics and said detection units.

3. The light scanning device according to claim 1, wherein the focussing optics is adapted to be radially displaced relative to an axis of rotation of the sample holding device.

4. The light scanning device according to claim 2, wherein the sample holder is adapted to be displaced in the radial direction relative to an axis of rotation of the focussing optics.

5. The light scanning device according to claim 1 or 2, wherein the detection unit and the focussing optics (34, 44) are coupled together and have, at least partially, a common optical path.

6. The light scanning device according to claim 4, wherein the focussing optics (34, 44) and the detection unit have a common beam splitter (33, 43) so as to unite or separate the optical paths of the excitation light and of the secondary light.

7. The light scanning device according to claim 6, wherein the beam splitter (33, 43) is a dichroic beam splitter which reflects either the exciting light or the secondary light and which essentially transmits the respective other light.

8. The light scanning device according to claim 6, wherein the beam splitter reflects the light incident thereon in a ratio of 50:50.

9. The light scanning device according to claim 1, or 2, wherein said focussing optics and detection unit pairs are mechanically coupled.

10. The light scanning device according to claim 1 or 2, wherein a pinhole diaphragm is arranged in front of the detector device in an imaging plane of the detection optics for the secondary light.

11. The light scanning device according to claim 1 or 2, wherein a blocking filter for suppressing the exciting light is arranged in front of the detector device.

12. The light scanning device according to claim 1 or 2, wherein the detector device (31, 41) and/or the light emission device (10) are arranged in a fixed manner.

13. The light scanning device according to claim 12, wherein the detector device and/or the light emission device are coupled to the detection optics and the focussing optics, respectively, for transmitting light via optical fibres.

14. The light scanning device according to claim 1 or 2, wherein a colour filter is provided in front of the detector device so as to transmit a specific wavelength of the secondary light.

15. The light scanning device according to claim 1 or 2, wherein the light emission device comprises a plurality of laser diodes each having a different output wavelength.

* * * * *

(12) EX PARTE REEXAMINATION CERTIFICATE (5716th)
United States Patent
Wulf et al.

(10) Number: US 6,211,989 C1
(45) Certificate Issued: Mar. 20, 2007

(54) LIGHT-SCANNING DEVICE

(75) Inventors: Jürgen Wulf, Ueberlingen (DE); Michael Steinwand, Owingen (DE); Henry Klemm, Ueberlingen (DE)

(73) Assignee: Bodenseewerk Perkin-Elmer GmbH, Ueberlingen (DE)

Reexamination Request:
No. 90/007,275, Oct. 29, 2004

Reexamination Certificate for:
Patent No.: 6,211,989
Issued: Apr. 3, 2001
Appl. No.: 09/367,949
Filed: Dec. 17, 1999

(22) PCT Filed: Dec. 4, 1997
(86) PCT No.: PCT/EP97/06793
§ 371 (c)(1),
(2), (4) Date: Dec. 17, 1999
(87) PCT Pub. No.: WO98/38495
PCT Pub. Date: Sep. 3, 1998

(30) Foreign Application Priority Data

Feb. 24, 1997 (DE) .......................... 197 07 226

(51) Int. Cl.
*G02B 26/08* (2006.01)

(52) U.S. Cl. .................. 359/210; 359/209; 356/317
(58) Field of Classification Search ......... 359/209–210; 356/317–320; 422/82.05–82.08; 250/458.1, 250/461.2
See application file for complete search history.

(56) References Cited

U.S. PATENT DOCUMENTS

| | | |
|---|---|---|
| 4,626,684 A | 12/1986 | Landa |
| 5,022,757 A | 6/1991 | Modell |
| 5,091,652 A | 2/1992 | Mathies et al. |
| 5,223,718 A | 6/1993 | Taboada et al. |
| 5,329,352 A | 7/1994 | Jacobson |
| 5,459,325 A | 10/1995 | Hueton et al. |
| 5,537,247 A | 7/1996 | Xiao et al. |

FOREIGN PATENT DOCUMENTS

| | | |
|---|---|---|
| EP | 0 392 475 A2 | 10/1990 |
| EP | 0 504 432 A1 | 9/1992 |

(Continued)

OTHER PUBLICATIONS

European Search Report dated Mar. 29, 2006, 5 pages.

(Continued)

*Primary Examiner*—James Phan

(57) ABSTRACT

A light scanning device for exciting and detecting secondary light, especially fluorescent light, on a sample, comprising a light emission device for emitting exciting light with a wavelength suitable for exciting secondary light on or in said sample, a focussing optics for focussing the exciting light on a subarea of said sample, a sample holding device for releasably holding the sample, a detection unit comprising a detection optics for the secondary light emitted by the sample in response to excitation and a detector device for converting the detected and imaged secondary light into electric signals. In the case of conventional known light scanning devices, scanning is carried out by means of a deflection unit consisting of tilting mirrors. Due to the long path of the light beam, positioning inaccuracies of the tilting mirrors result in major position inaccuracies of the scanning ray bundle on the surface of the sample. For avoiding this disadvantage of the prior art, the light scanning device according to the present invention makes use of a sample holding device which is adapted to be rotated for rotating the sample relative to the exciting light in such a way that different subareas of said sample can be excited by means of the exciting light so as to emit secondary light. Due to the mechanical rotary movement of the sample, a deflection of the scanning light beam relative to the optical axis is not necessary so that precise positioning of the scanning ray bundle on the sample is possible.

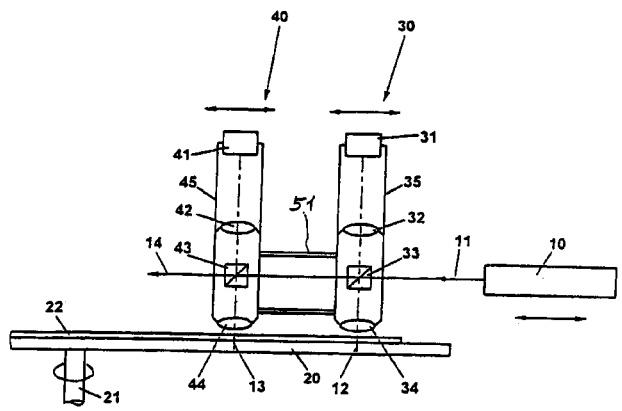

FOREIGN PATENT DOCUMENTS

| | | |
|---|---|---|
| EP | 0 753 779 A2 | 1/1997 |
| EP | 0 753 799 B1 | 10/2002 |
| JP | 02-203255 | 8/1990 |
| JP | 02-269938 | 11/1990 |
| JP | 05-142144 | 6/1993 |
| JP | 06-308030 | 11/1994 |
| WO | WO 96/09548 | 3/1996 |
| WO | WO 97/46712 | 12/1997 |

OTHER PUBLICATIONS

Official Letter mailed on Jun. 12, 2001, from Japanese Patent Application No. 1998–537203 (English language translation).

Official Letter mailed on Aug. 13, 2002, from Japanese Patent Application No. 1998–537203 (English language translation).

U.S. Appl. No. 09/367,949, Aug. 31, 2000 Office Action.

US 6,211,989 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–2 are determined to be patentable as amended.

Claims 3–15, dependent on an amended claim, are determined to be patentable.

New claims 16–52 are added and determined to be patentable.

1. A light scanning device for exciting and detecting secondary light, especially fluorescent light, on a sample (22), comprising
   a light emission device (10) for emitting exciting light (11) with a wavelength suitable for exciting secondary light on or in said sample (22),
   a [focussing] *focusing* optics (34, 44) for [focussing] *focusing* the exciting light on a subarea of said sample (22),
   a sample holding device (20, 21) for releasably holding the sample (22), and
   a detection unit comprising a detection optics (32, 42) for the secondary light emitted by the sample in response to excitation and a detector device (31, 41) for converting the detected and imaged secondary light into electric signals,
   wherein the sample holding device is adapted to be rotated for rotating the sample relative to the exciting light so that different subareas of said sample can be excited by means of the exciting light so as to emit secondary light, and
   there are at least two respectively associated pairs of said [focussing] *focusing* optics and said detection units.

2. A light scanning device for exciting and detecting secondary light, especially fluorescent light, on a sample (22), comprising
   a light emission device (10) for emitting exciting light (11) with a wavelength suitable for exciting secondary light, on or in said sample (22),
   a [focussing] *focusing* optics (34, 44) for [focussing] *focusing* the exciting light on a subarea of said sample (22),
   a sample holding device (20, 21) for releasably holding the sample (22), and
   a detection unit comprising a detection optics (32, 42) for the secondary light emitted by the sample in response to excitation and a detector device (31, 41) for converting the detected and imaged secondary light into electric signals,
   wherein the [focussing] *focusing* optics (34, 44) is rotatably supported so as to conduct the exciting light along a circular arc on the sample, and
   there are at least two respectively associated pairs of said [focussing] *focusing* optics and said detection units.

*16. A light scanning device for exciting and detecting secondary light on a sample, comprising*
   *a light emission device for emitting exciting light with a wavelength suitable for exciting secondary light on or in said sample,*
   *a sample holding device for releasably holding the sample, and*
   *at least two optical units, each optical unit respectively comprising*
      *a focusing unit comprising a focusing optic for focusing the exciting light on a subarea of said sample, and*
      *a detection unit comprising a detection optic configured to detect and image the secondary light emitted by the sample in response to excitation with the exciting light and a detector device for converting the detected and imaged secondary light into electric signals,*
   *wherein the light scanning device is configured to scan different subareas of the sample so that the different subareas of said sample can be excited by means of the exciting light so as to emit the secondary light,*
      *wherein the scanning comprises a relative movement between the sample and the focusing optic, and the light scanning device configuration comprising*
         *the sample holding device being adapted to be rotated for rotating the sample relative to the exciting light*
         *or*
         *the focusing optic being rotatably supported so as to conduct the exciting light along a circular arc on the sample.*

*17. A light scanning device according to 16, wherein, for each of the at least two optical units, at least one focusing optic is optically associated with the respective detection unit.*

*18. A light scanning device according to 17, wherein the optical association for each of the at least two optical units is mediated by respectively different dyes.*

*19. A light scanning device according to 16, wherein, for each of the at least two optical units, the focusing unit comprises at least one light emission device optically associated with the respective detection unit.*

*20. A light scanning device according to 16, wherein, for each of the at least two optical units, at least one focusing optic is mechanically associated with the respective detection unit.*

*21. A light scanning device according to 16, wherein, for each of the at least two optical units, at least one focusing optic is associated with the respective detection unit, the association comprising (i) an optical association mediated by respectively different dyes and (ii) a mechanical association.*

*22. A light scanning device according to 16, wherein each of the at least two optical units comprises separate detection units.*

*23. A light scanning device according to 16, wherein each of the at least two optical units comprises separate focusing optics.*

*24. A light scanning device according to 16, wherein each of the at least two optical units further comprises separate support bodies.*

*25. A light scanning device according to 16, wherein each of the at least two optical units further comprises (i) separate detection units, (ii) separate focusing optics, and (iii) separate support bodies, wherein each separate support body contains the respective separate focusing optics and separate detection units.*

26. A light scanning device according to 16, wherein the at least two optical units comprises at least one common optical component.

27. A light scanning device according to 26, wherein the at least one common optical component is the light emission device.

28. A light scanning device according to 26, wherein the at least one common optical component is a beam splitter configured to couple excitation light into each of the at least two optical units.

29. A light scanning device according to 16, wherein the at least two optical units have respectively different optical paths.

30. A light scanning device according to 16, wherein the relative movement between the sample and the focusing optics comprises circular and linear relative movements.

31. A light scanning device according to 16, wherein the relative movement between the sample and the focusing optics comprises a raster scan of the sample relative to the focusing optics.

32. A light scanning device according to 16, wherein the relative movement between the sample and the focusing optics comprises a circular arc scan of the sample relative to the focusing optics.

33. A light scanning device according to 16, wherein a first detection unit is configured to detect a first wavelength range of secondary light, and a second detection unit is configured to detect a second wavelength range of secondary light.

34. A light scanning device according to 33, wherein the first detection unit comprises a first optical filter configured to selectively direct a first fluorescent emission from the sample to a first detector device, and the second detection unit is configured to selectively direct a second fluorescent emission from the sample to a second detector device.

35. A light scanning device according to 16, wherein the device is configured to couple at least two different ranges of excitation wavelengths to the sample.

36. A light scanning device according to 35, wherein the light scanning device further comprises at least two light emission devices, and the at least two different ranges of excitation wavelengths are respectively emitted from the at least two emission devices.

37. A light scanning device according to 16, wherein the light scanning device further comprises at least two emission devices, and each of the at least two optical units is respectively associated with at least one emission device.

38. A light scanning device according to 16, wherein, for at least one optical unit, the focusing optic and the detection unit are located on a common side relative to a plane perpendicular to the sample.

39. A light scanning device according to 38, wherein, for at least one optical unit, the focusing optic and the detection unit have at least partially overlapping optical paths.

40. A light scanning device according to 16, wherein, for at least one optical unit, the focusing optic and the detection unit are located on opposite sides relative to a plane of the sample.

41. A light scanning device according to 16, wherein at least one of the focusing optics comprise at least one optical fiber having proximal and distal ends, wherein the at least one optical fiber is configured to couple the excitation light between the light emission device at the proximal end and the sample at the distal end.

42. A light scanning device according to 41, wherein the light emission device is in a fixed location relative to the light scanning device, and distal end of the at least one optical fiber is configured for the relative movement with respect to the sample and the focusing optic.

43. A light scanning device according to 16, wherein at least one of the detection units comprises at least one optical fiber configured to couple the secondary light to the detector device for the at least one detection unit.

44. A light scanning device according to 43, wherein the detector device is in a fixed location relative to the light scanning device, and a distal end of the at least one optical fiber is configured for scanning by relative movement with respect to the sample.

45. The light scanning device according to claim 16, wherein for at least one optical unit the detection unit and the focusing optic are coupled together and have, at least partially, a common optical path.

46. The light scanning device according to claim 45, wherein for the at least one optical unit the focusing optic and the detection unit have a common beam splitter so as to unite or separate the optical paths of the excitation light and of the secondary light.

47. The light scanning device according to claim 46, wherein the beam splitter is a dichroic beam splitter which reflects either the exciting light or the secondary light and which essentially transmits the respective other light.

48. The light scanning device according to claim 46, wherein the beam splitter reflects the light incident thereon in a ratio of 50:50.

49. The light scanning device according to claim 16, wherein for at least one optical unit a pinhole diaphragm is arranged in front of the detector device in an imaging plane of the detection optic for the secondary light.

50. The light scanning device according to claim 16, wherein a blocking filter for suppressing the exciting light is arranged in front of at least one of the detector devices.

51. The light scanning device according to claim 16, wherein for at least one optical unit a color filter is provided in front of at least one of the detector device so as to transmit a specific wavelength of the secondary light.

52. The light scanning device according to claim 16, wherein the light emission device comprises a plurality of laser diodes each having a different output wavelength.

* * * * *